United States Patent [19]

Ray

[11] Patent Number: 4,657,002
[45] Date of Patent: Apr. 14, 1987

[54] BONE IMPACTORS
[75] Inventor: Charles D. Ray, Deephaven, Minn.
[73] Assignee: Charles D. Ray, Ltd., Wayzata, Minn.
[21] Appl. No.: 731,024
[22] Filed: May 6, 1985
[51] Int. Cl.$^4$ .............................................. A61F 5/04
[52] U.S. Cl. .............................. 128/92 V; 128/92 VT
[58] Field of Search ............... 128/92 X, 92 YJ, 92 R, 128/92 XT, 92 XJ

[56] References Cited
FOREIGN PATENT DOCUMENTS
721086 3/1980 U.S.S.R. .

OTHER PUBLICATIONS
Mueller, Division of American Hospital Supply, Chicago, IL, catalog p. 108.

Primary Examiner—C. Fred Rosenbaum
Assistant Examiner—C. W. Shedd
Attorney, Agent, or Firm—Williamson, Bains, Moore & Hansen

[57] ABSTRACT

A bone impactor consists of a single piece of lightweight metal which has a handle and a smooth shank, across the tip of which extends a working surface that forms a symmetrical cylindrical concavity that may be fitted against an excrescence, followed by striking the butt end of the handle to compress the excrescence into the bone to relieve pressure on a nerve. The edges of the working surface are radiused to minimize cutting. That bone impactor preferably is one of a set of four, the working surface of the second impactor being rectangular and that of the third being circular, while the handle and shank of the fourth impactor have a uniform, rectangular cross section.

20 Claims, 7 Drawing Figures

BONE IMPACTORS

FIELD OF THE INVENTION

The invention concerns bone impactors which are useful for compressing bone excrescences to relieve pressure on a nerve and are especially useful for spinal decompression.

BACKGROUND ART

A major cause of spinal stenosis or entrapment of neural tissues is the presence of hyperostoses, bone spurs, disc bars, osteophytes, and other excrescences from bony or bony/ligamentous overgrowth. The usual surgical procedure for relieving the consequent compression of the neural tissues and attendant blood vessels is to cut off the excrescence with an osteotome or a high speed air drill. All bony structures have two principle layers: an outer hard layer called the cortex and a softer, spongy inner layer called the cancellous portion. If the cortical portion is cut away in order to eliminate an excrescence, this may weaken the bone, possibly promote an overgrowth of the cancellous portion and hence a return of the excrescence, or may leave an irregular surface against which the nerve must lie. Furthermore, bone is covered with membranes and often with ligaments which when cut away in the usual fashion (air drills and osteotomes) may leave behind ragged edges of the adherent soft tissues. This may promote fibrosis (scar tissue formation).

Among the most common locations for compression of nerve and blood vessels in the human spine is the area that lies adjacent to an oval structure known as the pedicle. Major nerves coming out of the spinal cord and its containing sac pass around and beneath the pedicle almost like a rope passing around a pulley. Overgrowth of a portion of the pedicle may produce nerve compression which may be relieved by cutting away the overgrowth, but the cutting of this overgrowth or of any other excrescence may be difficult and lead to complications. For example, upon cutting away a bone spur which is a mixture of calcific and soft tissue along the margins of a disc bar, the remaining surfaces may be quite irregular or torn, and this may lead to redevelopment of spurs or to epidural or perineural fibrosis. Furthermore, the neural tissue is usually in such close proximity to the spur that removing it presents a mechanical hazard.

OTHER PRIOR ART

I am aware of only one publication which suggests the use of a bone impactor to compress bone to relieve pressure on nerve tissue, namely U.S.S.R. Author's Certificate No. 721086 (V. T. Pustovoitenko) published Mar. 15, 1980 in Bulletin No. 10 and having a date of publication of Mar. 25, 1980. As shown in the drawing, the bone impactor has a curved tip which is inserted between the anterior wall of the dural sac and the posterior wall of the vertebral body by passing around the sac laterally. A notch in the curved tip of the bone impactor is placed over a prominent bony process or excrescence of a fractured vertebra. By striking the butt end of the bone impactor, a portion of said process is compressed. While that procedure should decompress the nerve tissue more easily and with less hazard than would cutting away the process, a fracture of this type which produces a nerve compression is rare. Hence, there would be very little use for the U.S.S.R. bone impactor.

Bone impactors are widely used for driving bone plugs and for packing bone chips. A catalog of Richards, Inc., Memphis, Tenn., shows a number of instruments which can be used as bone impactors, e.g., "Tibial Component Impactor", Catalog No. 11-0225, "Jewett Bone Chip Packers", Catalog No. 11-0991, etc., "T-Handled Elevator", Catalog No. 11-1148, and "Hob-nail Impactor", Catalog No. 11-1154, the working surface of which has a diamond knurl. A catalog of Codman Instrument Co. shows a Cloward "Bone Graft Impactor, double ended", Catalog No. 28-1000. None of those instruments would be useful for decompressing nerve tissue.

DISCLOSURE OF INVENTION

The invention provides a set of bone impactors by which a bone excrescence can be compressed instead of being cut away to relieve pressure on a nerve and associated blood vessels. One of the novel set of bone impactors comprises a handle and a shank, across the tip of which extends a working surface that forms a symmetrical cylindrical concavity, the axis of which extends at an angle of 50°–80° to the direction of attack of the impactor. By "direction of attack" is meant the direction in which forces are transmitted to an excrescence by striking the butt end of the handle. Each edge of the working surface should have a radius of at least 0.1 mm, preferably about 0.2 mm, to minimize cutting. Preferably the height of the cylindrical surface is less than the length of the chord between its circumferential extremities.

The working face of one of the novel set of bone impactors forms a cylindrical concavity, because the most common stenosis involves the inferior and medial aspect of the pedicle and a cylindrical concavity fits quite well into the usual contour of this portion of the pedicle. Because the working surface of the impactor is brought against the base of the pedicle from an acute angle, it would be difficult both to fit the concave working surface to the stenosis and to raise the handle of the impactor sufficiently to strike its butt end cleanly if the angle between the axis of the cylindrical concavity and the direction of attack were much greater than 80°. On the other hand, if that angle were much less than 50°, the acute arcuate edge between the circumferential extremities of the concave working surface might cause some cutting, even though having a preferred radius of about 0.2 mm. The handle and shank of the impactor preferably lie in a substantially straight line so that forces can be squarely transmitted to an excrescence by striking the butt end of the handle, thus minimizing any danger of slippage. However, the shank may be gently curved (similarly to, but preferably less abruptly than that of the aforementioned U.S.S.R. author's certificate) to facilitate reaching around a nerve which is to be relieved. When the handle and shank lie in a straight line, the face of the shank with which the cylindrical concavity makes an acute angle preferably is tapered inwardly toward the tip, while the opposite face is flat. This permits a higher elevation of the handle when the bone impactor is being used to repair the aforementioned common stenosis, thus making it easier to strike the butt end of the handle.

At least one of the set of bone impactors of the invention should have a flat working surface. For example, a second impactor of the set may have a small, flat rectangular working surface for impaction of spurs. A third impactor of the set may have an even smaller, flat circular working surface for driving or fracturing smaller segments of a spur which may later be impacted with a larger instrument. A fourth impactor of the set may have a handle and shank which are indistinguishable from each other, each having the same uniform, rectangular cross section, the area of which equals the area of the working surface at the tip of the shank. Knurls may be formed in a working surface of such a large area to reduce the danger of slippage during the impacting. The knurls preferably form concentric circles. An impactor with a large working area is useful for finishing or smoothing excrescences which have been impacted by one or more of the first three bone impactors, and also may be used to drive bone plugs or to fuse bone chips.

The four described bone impactors provide a complete set to deal adequately with nearly any excrescence. The shank of each of the impactors should be smooth so as not to injure tissues which it may contact. The handle and shank of each of the four impactors preferably are a single piece of lightweight metal such as aluminum having an anodized finish which is resistant to autoclaving. A lightweight metal gives the surgeon a better feel and makes accidental damage less likely.

Except for the third bone impactor of the set which has a circular working surface, the handle should be shaped to indicate the orientation of the working surface. A handle of uniform rectangular cross section is economical to manufacture and quite suitable for this purpose.

When the working surface of a bone impactor is small relative to the handle, the cross-sectional area of the shank should be substantially smaller than that of the handle, thus enhancing insertion of the shank into the incision and also minimizing visual interference.

Each edge of each working surface of the novel set of bone impactors should have a radius of at least 0.1 mm to avoid cutting any excrescence to be impacted.

THE DRAWING

The drawing illustrates a set of four bone impactors of the invention, each of which is a single piece of lightweight metal such as anodized aluminum. In the drawing.

Figure 1:
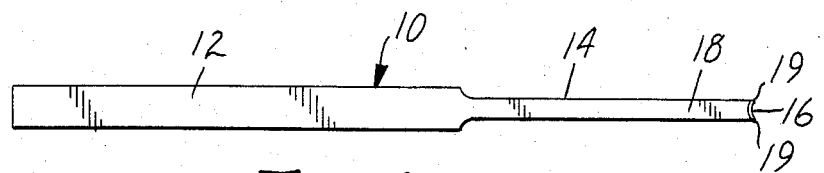
FIG. 1 is a top view of a preferred bone impactor of the invention.
Figure 2:
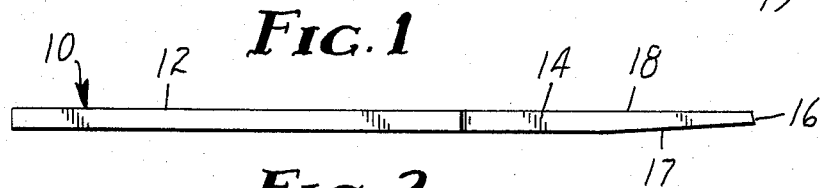
FIG. 2 is a side elevation of the bone impactor of FIG. 1.

The bone impactor 10 shown in FIGS. 1 and 2 consists of a handle 12 and a shank 14 which lie in a straight line. Across the tip of the shank is a working surface 16 which forms a cylindrical concavity. The axis of that cylindrical surface extends at an angle of about 70° with said straight line, namely, the direction in which forces are transmitted upon striking the butt end of the handle 12 while the concave working surface 16 is fitted against a bone excrescence. The face 17 of the shank 14 with which the concave working surface 16 makes an acute angle is tapered inwardly toward the concave working face, whereas the opposite face 18 of the shank 14 is flat over its full length for reasons explained above. In a prototype of the bone impactor 10, the handle 12 is about 15 cm in length, 1.1 cm in width, and 0.6 cm in thickness; the shank 14 is about 10 cm in length; the height of the cylinder formed in the working surface 16 is 0.3 cm; and the length of the chord between the circumferential extremities 19 of the cylinder is 0.6 cm.

Figure 3:
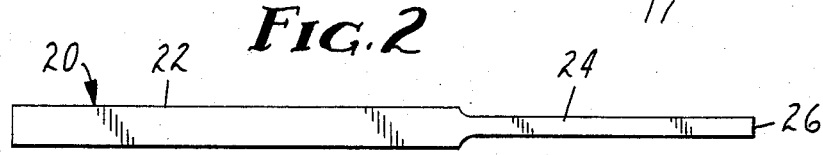
FIG. 3 is a top view of a second bone impactor of the invention.
Figure 4:
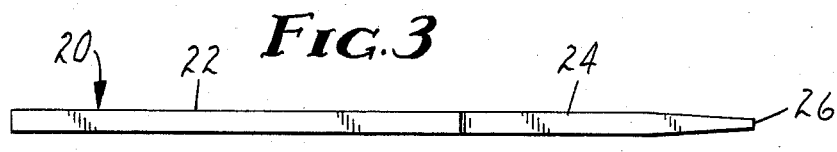
FIG. 4 is a side elevation of the bone impactor of FIG. 3.

The bone impactor 20 shown in FIGS. 3 and 4 has a handle 22 and a shank 24 which becomes smaller toward its flat, rectangular working surface 26. In a prototype of the impactor 20, the working surface 26 is 0.3 by 0.6 cm, with the long dimension extending in the same direction as the broad side of the handle 22.

Figure 5:
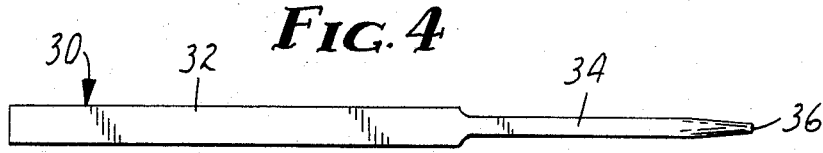
FIG. 5 is a top view of a third bone impactor of the invention.
Figure 6:
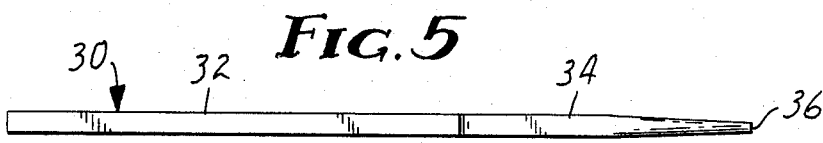
FIG. 6 is a side elevation of the bone impactor of FIG. 5.

The bone impactor 30 shown in FIGS. 5 and 6 has a handle 32 and a shank 34, across the tip of which is a small, circular working surface 36. In a prototype of the bone impactor 30, the diameter of the circular working surface 26 is 0.3 cm.

Figure 7:
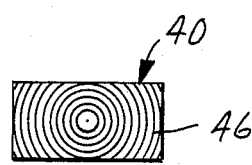
FIG. 7 is an end view, enlarged in comparison to FIGS. 1-6, showing the working surface of a fourth bone impactor which completes a set of bone impactors sufficient to compress almost any excrescence.

The handle and shank of the bone impactor 40 shown in FIG. 7 are of uniform cross section, and the flat working surface 46 at the tip of the shank is formed with knurls in concentric circles. In a prototype of the impactor 40, the working surface is 1.1 by 0.6 cm.

Each of the aforementioned prototypes is anodized aluminum, and the edges of the working surface of each prototype have been buffed, thus producing a radius of about 0.2 mm at each edge to minimize cutting upon impacting an excrescence.

The spinal surgical procedures for which the bone impactors of the invention are most needed involve lateral stenosis, and the areas of entrapment of nerve roots and ganglia are medial or inferior to the region of the pedicle. These areas are rather difficult to reach, expecially via approaches from the dorsal midline in the lumbar spine. Portions of the superior, lateral or inferior lamina must be removed in order to reach the nerve or ganglion and the associated, offending excrescence. Approaches from the far lateral direction may spare most of the posterior and lateral structures. The posterior unroofing of nerve, if needed, is usually accompanied by an anterior decompression such as the impaction of an osteophyte, ventral to the nerve.

The progression of approach to a lateral stenosis may involve the lamina and facet (dorsal to the nerve root), the vertebral body and spur (ventral to the nerve structures), and the pedicle (cephalad to the nerve structures). In this situation, following the more dorsal decompression from a rather lateral approach, the pedical may be moved away from the ganglion by cutting through the cancellous portion with an osteotome and then impacting the hard cortical portion into the partially resected cancellous portion. In this way, the medial and inferior portions of the pedicle (around which the nerve and ganglion must "wrap") are displaced away from the nerve to decompress it.

Another excellent application for impaction is along the posterior ridge of a disc bar. After removal of a bulging herniated disc, one may find that a rigid ridge remains quite prominently beneath the traversing nerve root or dural sac. In most such cases, impaction is a superior means for displacing the offending excrescence or disc bar from the nerve, leaving behind a relatively smooth surface. In a rather similar application, the disc bar and step-off of a spondylolisthesis may be impacted so that the nerve roots passing over the step will be relaxed and drawn over a much less acutely localized displacement against the ventral surface of the dural sac. Sometimes one may find the process of localized decompression easier to perform where the cortical surface is first fractured by one of the bone impactors and the remaining bone fragments lifted out.

I claim:

1. A bone impactor which is useful for compressing a bone excrescence to relieve pressure on a nerve and comprises a handle and a shank, across the tip of which extends a working surface that forms a symmetrical cylindrical concavity, the axis of which extends at an angle of 50°-80° to the direction of attack of the impactor, each edge of the working surface having a radius of at least 0.1 mm.

2. A bone impactor as defined in claim 1 wherein the height of the cylindrical concavity is less than the length of the chord between its circumferential extremities.

3. A bone impactor as defined in claim 2 wherein each edge of the concave working surface has a radius of about 0.2 mm.

4. A bone impactor as defined in claim 1, the handle and shank of which lie in a substantially straight line.

5. A bone impactor as defined in claim 4 wherein the face of the shank with which the concave working surface makes an acute angle is tapered inwardly toward the tip while the opposite face is flat.

6. A bone impactor as defined in claim 1 wherein said angle is about 70 degrees.

7. A bone impactor as defined in claim 1, the handle of which is shaped to indicate the orientation of the working surface.

8. A bone impactor as defined in claim 7, the shank of which is thinner than the handle and becomes smaller toward the tip.

9. A set of bone impactors, one of which is defined in claim 1, at least one other impactor of the set having a flat working surface, and each edge of its working surface has a radius of at least 0.1 mm.

10. A set of bone impactors as defined in claim 9 wherein the working surface of said other impactor is rectangular and its handle is shaped to indicate the orientation of the working surface.

11. A set of bone impactors as defined in claim 9 wherein the working surface of said other impactor is circular.

12. A set of four bone impactors, each consisting of a single piece of lightweight metal having a durable finish that is resistant to autoclaving, each of said pieces being shaped to have a handle and a smooth shank, across the tip of which extends a working surface, each edge of which has a radius of at least 0.1 mm, the working surface of a first of those impactors forming a symmetrical cylindrical concavity, the axis of which extends at an angle of 50°-80° to the direction of attack of the impactor, that of a second of those impactors being flat and rectangular, and that of a third being flat and circular, and the handle and shank of a fourth having a uniform, rectangular cross section.

13. A set of bone impactors as defined in claim 12 wherein the shank of each of the first, second and third impactors becomes smaller towards its tip.

14. A set of bone impactors as defined in claim 13 wherein the handle and shank of each impactor lie in a substantially straight line.

15. A set of bone impactors as defined in claim 14 wherein one face of the shank of the first of those impactors is tapered inwardly toward the tip while the opposite face is flat.

16. A set of bone impactors as defined in claim 15 wherein the working surface of the fourth of those impactors is flat and formed with knurls.

17. A set of bone impactors as defined in claim 12 wherein said lightweight metal is aluminum having an anodized finish.

18. Method of relieving pressure from a nerve caused by a bone excrescence comprising the steps of (1) forming a bone impactor having a handle and a smooth shank, the working surface which is a symmetrical cylindrical concavity, the axis of which extends at an angle of 50°-80° to the direction of attack of the impactor, (2) resting said working surface on the excrescence, and (3) striking the butt end of the handle to compress the excrescence into the bone.

19. Method as defined in claim 18 wherein the bone excrescence is on a pedicle of the spine, and step (2) involves fitting the working surface over the excrescence.

20. Method as defined in claim 19 wherein step (1) involves forming a second bone impactor to have a handle and a smooth shank which has a flat working surface extending across its tip, there being subsequent steps: (4) resting the flat working surface of the second impactor against portions of the impacted excrescence, and (5) striking the butt end of the handle of the second impactor to compress those portions into the bone.

* * * * *